United States Patent

Mericle

[11] Patent Number: 5,849,023
[45] Date of Patent: Dec. 15, 1998

[54] DISPOSABLE REMOTE FLEXIBLE DRIVE CUTTING APPARATUS

[76] Inventor: Robert William Mericle, 103 Morgan Rd., Eden, N.C. 27288

[21] Appl. No.: 773,417

[22] Filed: Dec. 27, 1996

[51] Int. Cl.⁶ .......................... A61B 17/14; A61B 17/32; A61B 17/00
[52] U.S. Cl. .............................. 606/180; 606/167; 606/79
[58] Field of Search .................................. 606/1, 107, 159, 606/166, 167, 170, 171, 180, 181, 79, 80; 408/8, 31, 124; 30/165, 388, 215; 407/30, 35

[56] References Cited

U.S. PATENT DOCUMENTS

Re. 34,556  3/1994  Sjostrom et al. ........................ 606/170

Primary Examiner—Glenn K. Dawson
Attorney, Agent, or Firm—Gipple & Hale; John S. Hale

[57] ABSTRACT

The present invention is directed toward an external drive with a plurality of removably mounted disposable surgical hand cutting assemblies including a housing control unit with a plurality of motors, each of the motors being capable of driving each surgical hand cutting assembly at a different range of rotational speeds.

One disposable surgical hand cutting assembly is capable of debriding soft tissue at a first speed and high torque, and a second disposable hand cutting assembly is capable of debriding hard tissue at a second higher speed.

A plurality of flexible shafts for transmitting the torsional force from a selected motor to a selected surgical hand cutting assembly provided with a quick connect mechanism disposed on the end of each flexible shaft to quickly connect the surgical hand cutting assembly to one of the motors.

18 Claims, 5 Drawing Sheets

DISPOSABLE REMOTE FLEXIBLE DRIVE CUTTING APPARATUS

FIELD OF THE INVENTION

The present invention generally relates to the field of tissue removal and more specifically relates to disposable handpieces for surgical tissue removal during ENT or orthopedic surgical procedures.

BACKGROUND OF THE INVENTION

Generally in the field of surgery, rotational and reciprocal cutting instruments have been used to sever tissue from a patient. Such instruments have encountered numerous problems and have had many shortcomings. The following patents constitute representative types of prior art instrumentation directed toward tissue removal.

U.S. Pat. Nos. 5,456,689 and 5,527,331 to Kresch et al. disclose a tissue resection instrument including a rigid shaft having a profusion lumen and fiber optic scope. A drive tube is rotatably disposed within the rigid shaft lumen and includes a drive tube aspiration lumen. A D.C. motor is located in the handpiece housing and is coupled with the drive tube by a belt and toothed pullies to rotate the drive tube and thus rotate a cutting head.

U.S. Pat. No. 4,490,859 to Mische et al. discloses an intravascular occlusion material removal device for removing vascular occlusion material in a vascular lumen. A flexible drive shaft is operatively connected to an expandable material removal element to rotate the removal element. The device includes a hand held housing which contains an electric motor, a power source and a switch on the outside of the housing for controlling the motor and associated drive shaft revolution speed.

U.S. Pat. No. 5,437,630 to Daniel et al. shows a powered rotatable surgical cutter with the motor in the handle and includes a connection to a suction source. The tool has a tubular elongate outer member having a distal tip portion angled off the central axis of the proximal portion of such tubular outer member by reason of an angled portion. A rotatable elongate inner member extends coaxially and rotatably within the tubular outer member and has a rotatably driveable proximal portion, a distal tip portion for tissue working interaction with the distal tip portion of the outer member and a flexibly bendable portion. The flexible portion of the rotatable shaft is comprised of a plurality of flexible coils of wound wires wrapped around at least one coaxial central wire.

U.S. Pat. No. 5,411,514 to Fucci et al. discloses a surgical cutting instrument having a rotatable flexible inner cutting member adapted to rotate within a flexible outer tube. The rotatable inner shaft is provided with a flexible section adjacent its distal end which enables the distal end of the inner shaft to be bent in a desired angle while still permitting a cutting member disposed at the distal end to rotate.

U.S. Pat. No. 5,383,884 issued to Summers discloses a spinal disc surgical instrument comprising a handle and a cannula shaft extending therefrom with a drive shaft extending through a bore in the handle and through the cannula shaft. The distal end of the drive shaft incorporates a cutter with an auger-like profile for shaving herniated discs. The cutter transports the shaved segments backward towards an annulus formed between the cannula shaft and the drive shaft.

A single motor surgical system for operating a set of different surgical devices at different rotational speeds is disclosed in reissued U.S. Pat. No. Re. 34,556 to Sjostrom et al. The preferred embodiment of the system includes an arthroscopic handpiece adapted to receive different removable rotary tip assemblies. The system consists of a handpiece containing a motor which is adapted to selectively receive several surgical devices, each device having an indicator on its proximal portion which denotes its operational limit. The handpiece includes an automatic sensor for sensing the indicator and controls responsive to the sensor to automatically establish the operational limit of the motor in accordance with the respective surgical device received by the handpiece.

U.S. Pat. No. 5,286,253 to Fucci discloses a thin walled sleeve of polymeric or similar material which is heat shrunk or otherwise closely fitted over a flexible torque-transmitting shaft with a cutter member. The flexible shaft is mounted in an angled rigid outer sheath which is mounted in a handpiece holding the drive motor, the torque-transmitting shaft being operably connected to the motor shaft.

U.S. Pat. No. 5,242,460 to Klein et al. discloses atherectomy catheters which have cylindrical cutting heads rotatably mounted at the distal ends of the bodies of the catheters. Each head has an axially elongated aperture and an open interior. A preferred embodiment has the elongated aperture helically disposed about the central axis of the cylindrical head and a cutter mechanism formed integrally along the periphery of the aperture.

A dilation catheter for reopening blood vessels is disclosed in U.S. Pat. No. 5,201,750 to Hocherl et al. The dilation catheter is insertable through vessels to lead to the constriction point and has a working head for widening the vessel constriction. An electrical, battery driven motor is contained within the housing of the unit and a toothed belt is used to rotate the spindle of the catheter.

Another catheter is disclosed in U.S. Pat. No. 4,729,763 to Henrie. This patent discloses a catheter for removing occlusive material from the stenosis of a blood vessel. Other surgical devices having curved members variously referred to as stems, tubular members, or sleeves which hold the cutting means of the various devices are disclosed, respectively, in U.S. Pat. No. 1,630,239 to Binkley et al., U.S. Pat. No. 4,646,738 to Trott, and U.S. Pat. No. 4,644,951 to Bays. Patents illustrating surgical cutting devices having vacuum suction and rotating cutter heads include U.S. Pat. No. 5,135,531 to Shiber, U.S. Pat. No. 4,368,734 to Banko, U.S. Pat. No. 4,445,509 to Auth; U.S. Pat. No. 4,461,305 to Cidley and U.S. Pat. No. 4,466,429 to Loscher et al.

A major problem with surgical cutting devices presently used is that they have a high failure rate because of the effects of the sterilization process on the mechanical functioning of the drive motor and structure of parts of the handpiece.

Other problems exist in the present state of the art handpiece cutters such as the inability of some of these surgical instruments to provide the surgeon with the means to both remove fluids and particulate matter from the surgical site and also provide a stream of fluid to the site to clean the area and cool the cutter blade. Other shortcomings of these cutter handpieces is that they generally lack the capability of providing the surgeon with the ability to use the handpiece with a relatively low speed, high torque electrical motor and to quickly and easily switch to a relatively high speed, low torque electrical motor.

The present inventive surgical cutting apparatus solves these and other problem in the known cutter designs and provides other advantageous features which will be described and illustrated hereinbelow.

SUMMARY OF THE INVENTION

The inventive surgical handpiece of the present invention is comprised of a disposable, lightweight assembly which can be provided to the surgeon in a sterile, sealed package for immediate use in surgery and disposed of after surgery. The disposable handpiece has a streamlined housing which serves as the handpiece for a flexible drive shaft which is designed to be quickly connected to the shaft of a drive motor which is located in a distal separate housing. The assembly also includes one or more other tubes which can be used to deliver sterile fluids to the surgical site or vacuum debris from the surgical site.

The cutting of the tissue at the surgical site can be performed by rotating a cutter tube or a drill or burr extending from the distal end of the handpiece. The rotating inner cutter tube is surrounded by a stationary outer cutting tube which is provided with an appropriately positioned aperture at the distal end thereof to interact with the shear walls of the inner cutter tube. The cutting device on the handpiece can either be directly driven by a flexible drive shaft or indirectly driven by the flexible shaft and a plurality of gears. The gear driven handpiece embodiment can be used with the hollow, rotating inner cutting tube to provide a means for removing debris from the surgical site by vacuuming the debris through the inside of the cutting tube toward the handle of the device and then out through a tube connected to the proximal end of the rotating cutting shaft out the proximal end of the handpiece housing. The handpiece with the gear embodiment also may be constructed with a reduced gear to permit higher drive shaft speeds if desired. The indirectly driven handpiece can include means for delivering sterile fluid to the surgical site.

Commonly used cutting devices generally require the device or the handpiece to be in such close proximity with the drive motor that the motor must always be sterilized between patients. If electrical motors are included in the handpiece, the temperatures, and/or chemical solutions and gases involved in the sterilization process often damage these motors, shorten their useful life spans and result in an increase in the failure rate. Other mechanical parts such as the bearings used to facilitate the rotation of certain handpiece parts are damaged by sterilization because the lubricants used on the bearings typically dissipate or breakdown under the conditions necessary to sterilize the instrument. Another common problem is that expensive duplicate sterilizable cutting devices have to be purchased by the user to allow for down time during sterilization. The present invention thus reduces capital costs and promotes medical cost efficiency.

The present invention solves this problem because it places the motor within a separate housing and control unit distal from the surgical site and thus eliminates the need to sterilize the electrical motor. The present invention also features a remote control unit which may be in the form of a foot pedal control which activates and controls the directional speed of two or more electrical motors. One electrical motor has a relatively low speed and high torque so that this motor can be used for cutting soft body tissues while the other motor is a high speed motor for drilling and grinding with burrs on the tip of the handpiece for cutting and shaping hard bone. The dual motors in one housing eliminate the need for two control units within the operating room and the need for constantly changing the cutting tip of the surgical device. The remoteness and non-sterile environment of the motor permits the use of a significantly lower cost motors.

It is an object of the invention to provide the surgeon with a low cost, disposable surgical handpiece which can be used once in one surgical procedure and then discarded under standard medical disposal procedures.

It is another object of the invention to provide the surgeon with a surgical handpiece cutter which does not contain an electrical motor within the housing of the handpiece so that the electrical motor can be located in a position remote from the surgical area in a non-sterile environment which would allow the motor to have a much longer life expectancy because it would not be subjected to the temperatures, chemicals and pressures involved in the sterilization process.

Yet another object of the invention is to provide a surgical handpiece cutter which can be used with either a high speed motor or low speed motor having selected torques for cutting either soft tissue or hard tissue, respectively. It is a further object of the invention to provide the user with a low cost control unit which contains a plurality of motors to enable the surgeon to select among a variety of motor speeds and torsional ranges.

Still another object of the invention is to provide a single motor housing containing a plurality of motors and a plurality of handpieces each connected to a motor and a control means to enable the surgeon to quickly and easily activate the selected handpiece.

Another object of the invention is to provide the surgeon with a streamlined pencil shaped handpiece which is easy to use, reduces hand fatigue and accommodates a wide range of cutting techniques.

A still further object of the invention is to provide a means of delivering sterile fluid to the surgical site or optionally removing debris from the surgical site via a vacuum source through a disposable cutting assembly which can be discarded after surgery.

Another object of the present invention is to provide the user with a surgical handpiece which requires no disassembly, no cleaning, and no sterilizing.

It is also an object of the present invention to provide the surgeon with a device which contains no electronics in the handpiece so there is no danger of electrical shock to the patient; the electronics being completely isolated from the handpiece.

Still another object of this invention is to provide the surgeon with a new handpiece and cutter for each patient to reduce the possibility of cross contamination between patients.

Yet another object of the present invention is to provide a disposable handpiece which either incorporates gears to drive the cutting tip or which directly couples the cutting tip to the drive source.

Finally, the non-motorized handpiece of the present invention will be the smallest, the lightest and the most powerful handpiece available to the surgeon. The remote location of the handpiece from the motor minimizes the size and weight of the handpiece and results in a more comfortable, pencil-like design. This will improve surgeon comfort by thus reducing the weight and will improve surgical visibility by reducing the size.

In the accompanying drawings, there is shown an illustrative embodiment of the invention from which these and other objectives, novel features and advantages will be readily apparent.

DETAILED DESCRIPTION OF THE INVENTION

Figure 1:
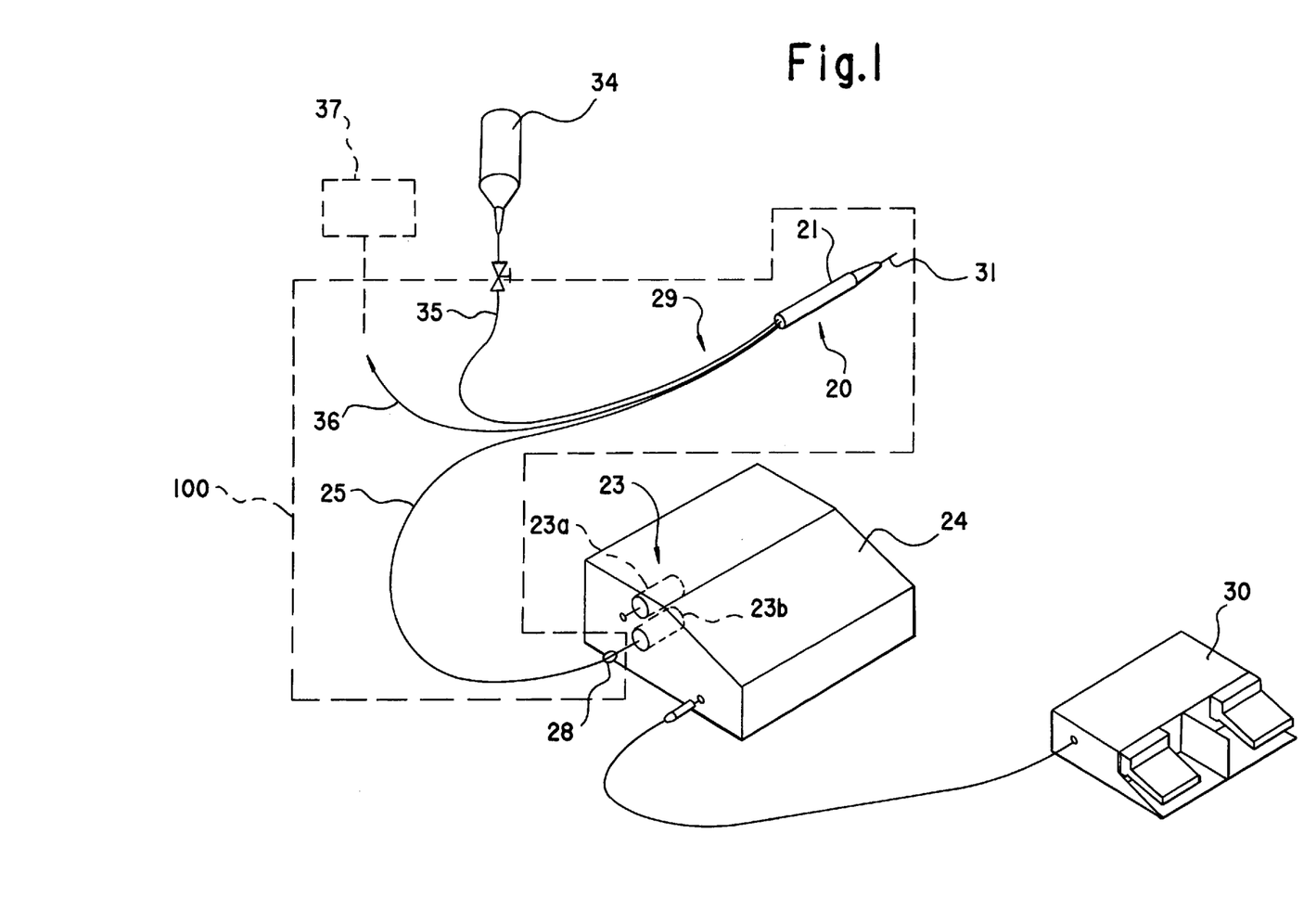
FIG. 1 is a perspective schematic view of the disposable surgical handpieces with flexible shafts shown schematically connected to a sterile fluid source, vacuum, and motor drive unit.
Figure 5:
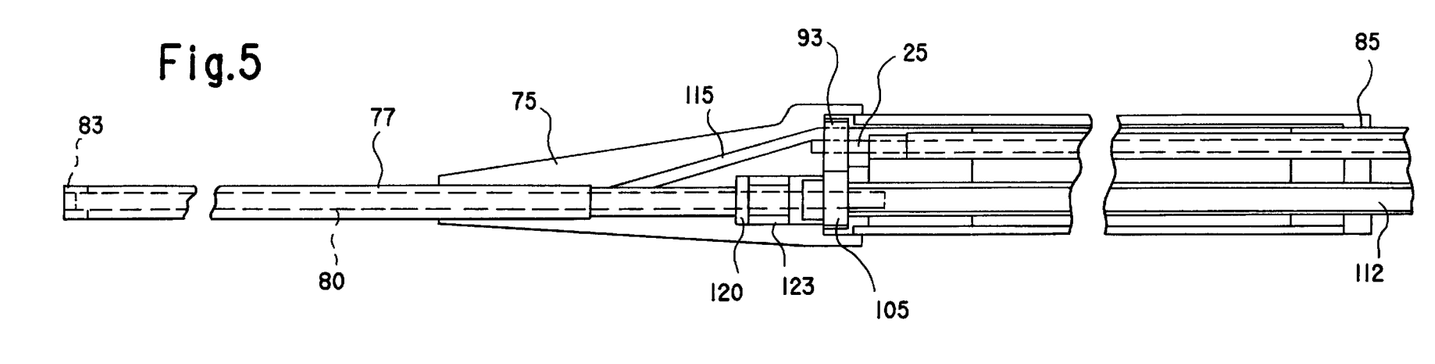
FIG. 5 is an enlarged side elevational view of the assembled gear driven handpiece shown in FIG. 4.
Figure 6:
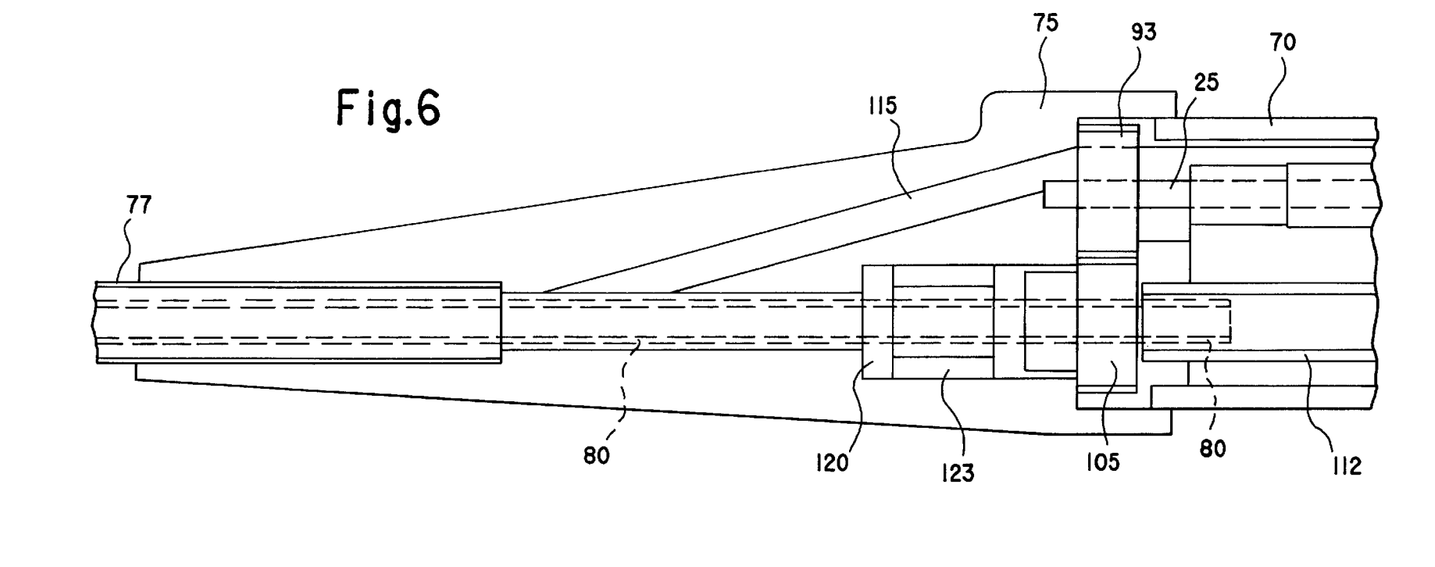
FIG. 6 is an enlarged portion of the gear drive section of the handpiece shown in FIG. 5.
Figure 7:
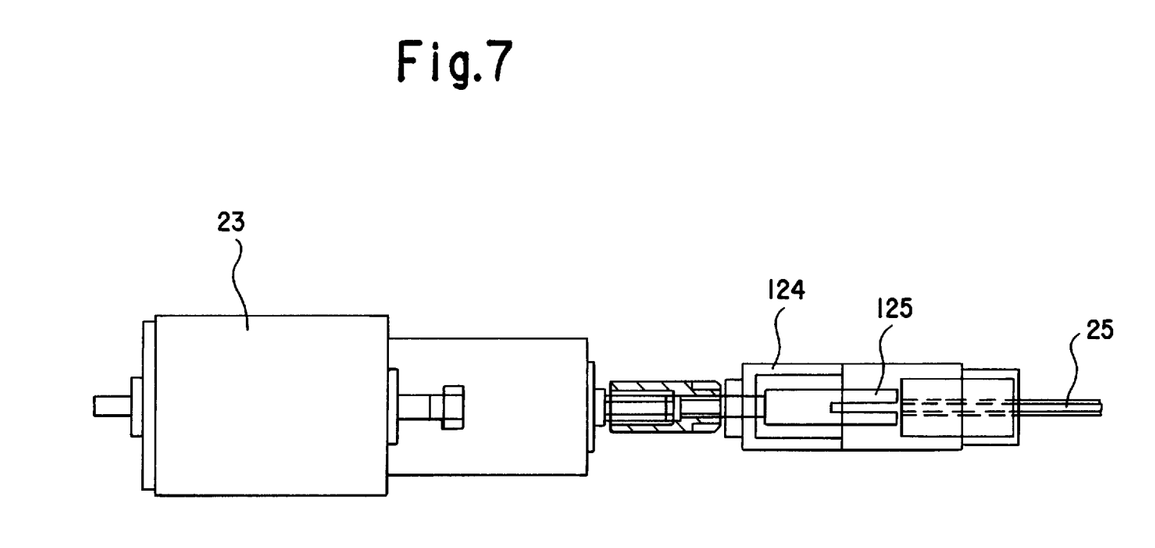
FIG. 7 is a side elevational view of a motor used to drive the handpiece showing the quick connect/disconnect coupling means for attaching the flex-shaft to the drive shaft of the motor.

The preferred embodiment and the best mode of the invention is shown in FIGS. 1 and 4–7. FIG. 1 shows the schematic configuration of the handpiece, flexible drive, drive motor housing and foot pedal control in place in the operating room. In accordance with the invention, the surgical handpiece assembly 20 is shown in FIG. 1 connected to an electric motor assembly 23, which is located inside a motor housing 24. The handpiece 20 is coupled to one of the motors 23b through the flexible drive shaft 25, also called the flex-shaft. The flex-shaft 25 is coupled to the drive motor 23 through a standard quick coupler mechanism 28 which is shown in FIG. 7. This quick coupling mechanism 28 allows the surgeon or operating room nurse to easily attach and remove the handpiece assembly from the motor. The flex-shaft 25 is long enough that the motor 23 can be placed remote from the patient so that it need not be placed within the sterile surgical environment. The motor housing can be further protected by placing the same in a sterile plastic bag or sheath. Consequently, the drive motor need not be sterilized between patient operations.

The inventive disposable surgical handpieces 20 of the present invention can be used selectively with a single multiple motor housing 24. This offers the surgeon and the hospital several advantages. When several handpieces 20 having different properties are required during an operation they are immediately accessible to the surgeon. The single motor housing configuration minimizes the space required for the motor housing 24, places the drive in a single stationary position, reduces the amount of time required to sterilize the operating room between procedures and enables a single control unit 30 to control several handpieces.

The disposable surgical handpiece assembly 20 is provided to the surgeon in a sterile, sealed package 100 with the handpiece 21, flex-shaft 25 and a plurality of tubes 29 such as a vacuum tube 36 and fluid feed 35 tube attached. The surgeon opens the package immediately before surgery, attaches the flex-shaft 25 through the quick disconnect 28 to the selected motor, tube 36 to the vacuum source 37 and fluid feed tube 35 to a saline bottle 34 and begins the surgical procedure. When the operation is finished, the handpiece 21, cutting tip 31, tubes 29 and flex-shaft 25 can be discarded into an operation room red bag or through normal medical disposal procedures. The plurality of tubes 29 which extend from the proximal end of the handpiece 21 are assembled with the handpiece as a single package to allow the surgeon to quickly connect the handpiece 21 to a source of sterile fluid 34 such as a saline bottle through a fluid tube 35 and to a vacuum source 37 through the vacuum tube 36. The vacuum source 37 is shown in the diagram schematically and is typically available in the operating room. FIG. 1 shows a broken line surrounding the disposable inventive handpiece assembly 20. This disposable portion of the surgical equipment therefore comprises the handpiece 21, associated tubes 35 and 36, the flex-shaft 25 and the associated quick connect/disconnect connectors on the shaft. This design enables the motors 23 within the housing 24 and the foot control 30 to be far enough away from the patient that they need not be sterilized between surgical procedures.

Figure 2A:
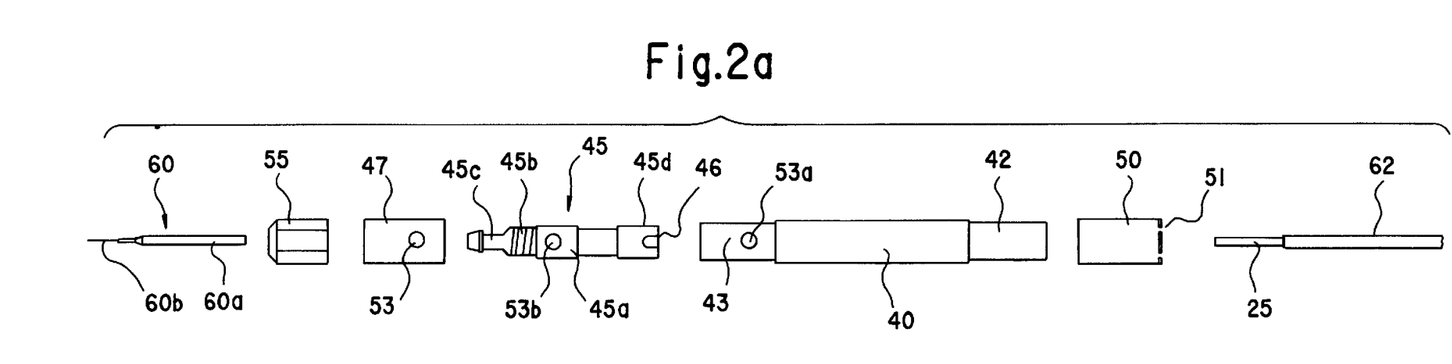
FIG. 2 is a exploded view of an embodiment of the flexible shaft direct drive handpiece.
Figure 2B:
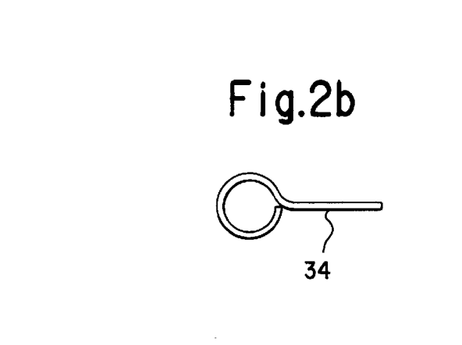
Figure 3:
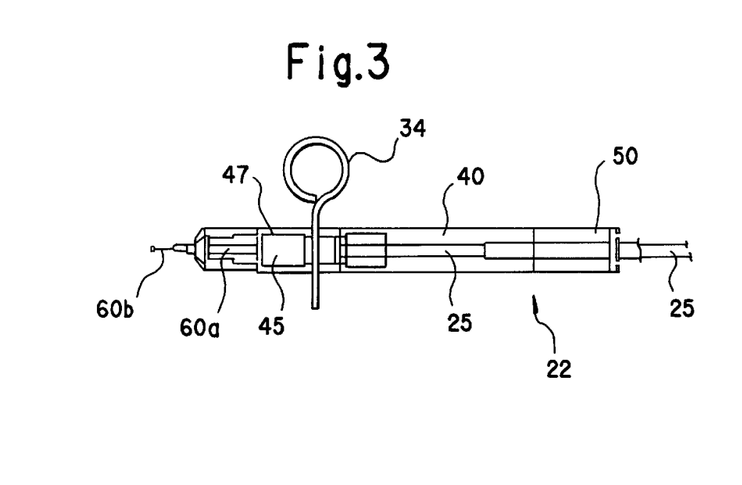
FIG. 3 is a side elevational view of the assembled handpiece shown in FIG. 2.

The flex-shaft 25 can drive the cutter directly or through a series of gears. The direct drive handpiece embodiment 22 is shown in detail in FIGS. 2 and 3. FIG. 3 shows the assembled direct drive handpiece 22 with a chuck pin 34 extending laterally through it. The chuck pin 34 holds the assembly together as will be later described when the retaining nut 55 is screwed onto the assembly. The direct drive handpiece 22 generally consists of a cylindrical housing 40 having a throughgoing bore having a proximal recessed or axially stepped portion 42 and a distal recessed or axially stepped portion 43. A rear portion of a split collet 45 is contained within the bore of the handpiece housing 40 in the assembled handpiece 22. The split collet 45 is generally constructed with a cylindrical midsection 45a, an externally threaded neck portion 45b, a cutting tool receiving distal tip of the collet 45c and a drive receiving section 45d. The collet 45 has a square collet bore 46 in its distal drive receiving section end 45d to receive the flexible shaft rod end 25 which has a square cross section. A cylindrical distal ferrule 47 with a throughgoing bore 53 has appropriate dimensions to fit on the distal recessed portion 43 of the handpiece housing 40 so that bore 53 is axially aligned with housing bore 53a. The distal ferule 47, the split collet 45 and the distal recessed portion 43 of the handpiece housing 40 are each respectively provided with chuck pin bores 53, 53b and 53a which, when the distal ferule 47 and the split collet 45 are mounted in place on the handpiece housing 40, are aligned to form a throughgoing bore or channel from one side of the handpiece housing to the other to accommodate the chuck pin 34.

The chuck pin 34 is used to hold the rotatable portion of the handpiece 22 in place while the threaded retaining nut 55 is screwed into place on the collet threaded neck portion 45b. The threaded retaining nut 55 has a hexagonal cross section which facilitates tightening the nut 55 onto the threaded neck portion of the split collet. The threaded retaining nut 55 is used to hold the shaft 60a of the cutting tool in place within the receiving tip 45c of the split collet. When the direct drive handpiece 22 is assembled, the collet 45 is disposed within the distal end portion of the bore in the handpiece housing 40 with sections 45b and 45c protruding from the end thereof as shown in FIG. 3. The distal ferule 47 is placed around the recessed portion of the handpiece 43 and the shaft of the cutting tool 60a is inserted within a bore, which is not shown between the split sections of the collet 45. The chuck pin apertures 53a, 53b, and 53 in the handpiece housing 40, the collet 45 and the distal ferrule 47 are aligned and the chuck pin 34 is inserted through the aligned bores so that it extends through the housing with the end of the chuck pin 34 emerging from the side opposite that from which it entered as shown in FIG. 3. The chuck pin 34 prevents the rotation of the collet 45 while the threaded retaining nut 55 is threaded on the threaded neck 45b of the collet and tightened. As the threaded retaining nut 55 is tightened on the collet 45, the bore in the distal tip of the collet 45c tightens around the shaft 60a of the cutting tool 60 to hold it in place.

The flex-shaft 25 is surrounded by a flex-shaft sheath 62 in both the direct drive and indirect drive embodiments. The flex-shaft 25 can be realized in a variety of forms in this invention. For example, a preferred configuration of the flex-shaft 25 consists of a flexible coaxial metal rod having a round cross section within a plastic tube, or with squared end surrounded by a spiraling wire for a major portion of its length to maintain the stability of the shaft during rotation. An example of this structure is a common speedometer cable. The flex-shaft 25 enters the proximal end of the handpiece 22 and is securely held in place in the square bore 46 in the collet 45 by sonic welding, adhesive, mechanical pin means or other suitable securing device known in the prior art. The proximal recessed or stepped portion of the handpiece housing 42 accommodates the proximal ferrule 50 which has a ferrule rear wall 51 to seal the proximal end of the handpiece housing 40. The proximal ferrule rear wall 51 is provided with an aperture which is not shown in the figures to allow the flex-shaft 25 to engage the collet.

In operation, the housing 40 of the direct drive handpiece and the two ferrules 47 and 50 do not rotate when the flex-shaft 25 is used to rotate the collet 45, the threaded retaining nut 55 and the cutting tool 60.

Figures 4, 4C, 4D:
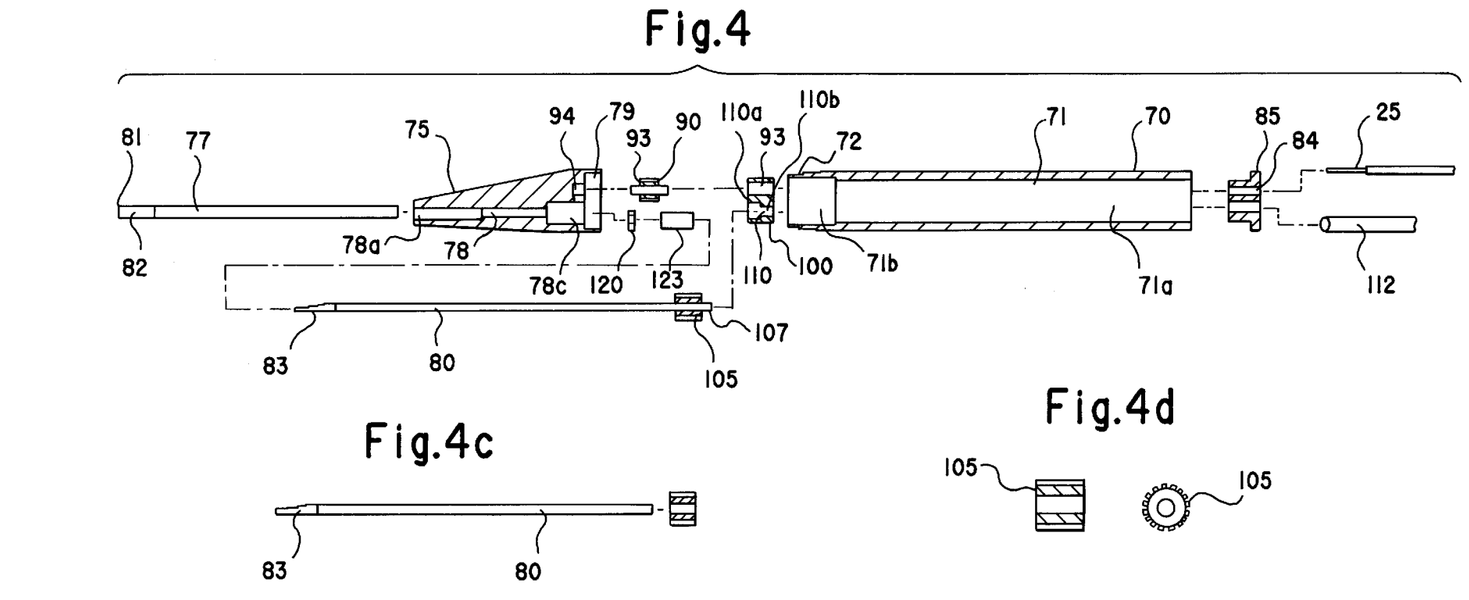
FIG. 4 is an exploded view of an embodiment of the flexible shaft gear driven handpiece.
FIG. 4c is an exploded view of the cutter tube and driven gear shown in FIG. 4.
FIG. 4d is an enlarged cross section and end view of the driven gear.

The geared handpiece 21 is shown in FIGS. 4–6. The main housing 70 of the geared handpiece has a thoroughgoing lumen 71 with a wider stepped diameter distal portion 71b and a narrower diameter proximal portion 71a. The distal end of the main housing 70 also has a tapered neck section 72 to accommodate the nose cone 75. An outer cutting tube 77 extends from the distal end of the nose cone 75 and is mounted in a cone bore section 78a. The nose cone 75 has a stepped throughgoing nose cone bore 78 which extends from the distal tip of the nose cone to a seat 79 which receives the recessed neck portion 72 of the main housing 70 allowing the nose cone to be removably secured to the housing.

The outer cutter tube 77 extends into the distal end of the nose cone bore in a stepped area 78a of the bore 78 and is held securely therein. The outer cutter tube 77 has a cutter tube lumen and a semi-rounded closed tip 81 with a cut out 82 on its distal end. An inner rotating cutting tube 80 with a cutting blade 83 having a serrated cutting surface and semi-rounded closed tip at its distal end extends through the nose cone bore 78 and through the length of the outer cutter tube 77. The outer cutter tube 77 is provided with a lateral opening 82 which allows the blade 83 to cut selected tissue which comes into contact with the distal end of the outer cutter tube 77 by shearing the tissue between a fixed tube wall and a rotating tube wall. The geared handpiece is provided with a passage through the main housing 70 to provide passage for a means for rotating the cutter blade, and to provide a container for tubing leading to a plurality of separate channels for delivering sterile fluid to the surgical site and removing excised tissue from the surgical site and out the proximal end of the handpiece to a waste storage receptacle.

The cutter blade 83 and its associated shaft 80 are rotated by the flex-shaft 25 through a plurality of interconnected gears. The flex-shaft 25 enters the proximal end of the main housing 70 through an off-set bore 84 in the rear plug 85 of the main housing 70. The square end of the flex-shaft 25 is held within a flex-shaft blind bore 88 in the axle 93 of the flex-shaft drive gear 90. The flex-shaft drive gear 90 is mounted on a drive gear axle 93 which supports the gear 90 while it is being rotated. The distal end of the drive gear axle 93a is rotatably held within a flex-shaft drive gear blind bore 94 formed in the proximal end of the nose cone 75. The proximal end of the drive gear axle 93b is rotatably mounted within a cylindrical drive gear axle shaft bore 98 formed in the gear outer bearing ring 100. The gear outer bearing ring 100 is held within the enlarged distal lumen portion 71b of the main housing lumen or bore. The flex-shaft 25 which is of the same construction as previously discussed enters the flex-shaft bore 84 in the rear plug 85, extends through the cylindrical shaft bore 98 in the gear outer bearing ring 100 and engages the square blind bore 88 of axle portion 93b to rotate the flex-shaft drive gear 90 which is fixed mounted on axle 93. The axle 93 is rotatably held in the nose cone bore 94 and the cylindrical shaft bore 98 in the gear outer bearing ring 100.

The proximal end of the inner cutting shaft 80 is in turn provided with a driven gear 105 which is mounted on shaft 80 by key means or other suitable means known in the art. The driven gear 105 has teeth which engage the flex-shaft drive gear 90 and is driven when gear 90 is rotated. The proximal end of the inner cutting tube 80 extends slightly beyond the proximal end of the inner cutting tube driven gear 105 to form a cutter shaft axle 107 for the cutter shaft driven gear 105. The gear outer bearing ring 100 is provided with a cutter shaft bore 110 to position axle 107 and facilitate the rotation of the inner cutter tube 80. The cutter shaft bore 110 has a wider distal cylindrical portion 110a and a narrower stepped proximal portion 110b. The narrower proximal portion 110b of the cutter shaft bore accommodates the proximal end of the inner cutting tube which functions as the axle 107. This structure enables the inner cutter tube 80 to be rotationally disposed within the outer cutter tube 77 for a bi-directional rotation of the cutter blade 81 at the end of the inner cutter tube 80.

Figure 4A:
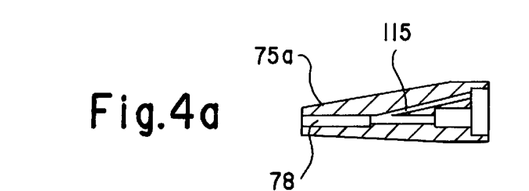
FIG. 4a is a cross section of the nose cone of the handpiece shown in FIG. 4.
Figure 4B:
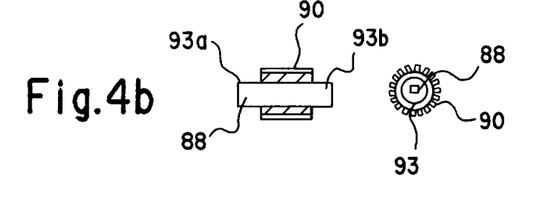
FIG. 4b is an enlarged cross section and end view of the drive gear axle shown in FIG. 4.

The outer surface of inner cutting tube 80 and the inner surface of the outer cutting tube 77 cooperate to form a cylindrical channel for the passage of sterile fluid to the surgical site. The sterile fluid is transported via a tube to channel 115 of the nose cone into the concentric cylindrical channel formed by the cutting tube. The inner cutter tube 80 has a longitudinal lumen which provides a means for removing debris from the surgical site. A vacuum tube 112 is positioned around the proximal end of the inner cutter tube 80 as best seen in FIG. 6 to provide the necessary suction force to remove excised tissue and excess fluids through the lumen of the cutter shaft 80 from the surgical site. Fluid or saline enters the handpiece 70 via a tubing 35 through a separate channel dedicated to the delivery of surgical fluid. The nose cone 75 is provided with a saline channel 115 as shown in FIG. 4a to receive the fluid and deposit the same at the beginning of channel 78 into the concentric channel formed between the outer diameter of the cutter shaft 80 and the inner diameter of the cutting tube 77 and thus outward into the surgical site.

An O-ring 120 is provided in the nose cone bore 78 to prevent the sterile surgical fluid which passes from saline channel 115 through the cylindrical channel formed between the outer cutting tube 77 and the inner cutting tube 80 from back flowing in a proximal direction into the handpiece housing. The O-ring 120 forms a water tight seal which retains the fluid forward of the proximal end of the surgical handpiece. The O-ring 120 is held in place in the nose cone bore 78c by an O-ring retainer 123.

The high speed low torque motor 23b in the housing 24 is a variable speed motor capable of rotating the flexible shaft coupled therewith at any rotational speed from zero to 16,000 revolutions per minute (rpm). The low speed, high torque electrical motor 23a also mounted in the housing has a range of rotational speeds which varies from zero to 800 revolutions per minute. All of the electronics in the power control unit are 115 volt AC to DC.

The electrical motors 23 within the motor housing 24 are bi-directional, variable speed devices which are controlled by the surgeon using the foot control 30. Foot control 30 is provided with a plurality of pedals 33 which are used to control the direction of rotation and operation of the cutting tip on the surgical handpiece assembly 20. A representative motor and quick connect/disconnect assembly are illustrated in FIG. 7. The shaft of the motor has a female quick disconnect 124 to receive a male connection 125 on the disposable flex-shaft 25.

Because the electronics are electrically isolated within the motor housing and the foot pedal housing, they do not come in contact with the patient. As previously noted both housings can be covered with a protective sheath. Therefore, the patient cannot be accidentally shocked and the motor does not have to be sterilized. The foot control does not need to be sterilized between patients because it also is remote from the patient.

In the forgoing description, the invention has been described with reference to a particular preferred embodiment, although it is to be understood that specific details shown are merely illustrative, and the invention may be carried out in other ways without departing from the true spirit and scope of the following claims:

I claim:

1. A surgical tissue cutting assembly comprising:
    a motor control unit comprising a plurality of motors, each of said motors being adapted to operate in a different operating range of rotational speeds;
    control means for controlling the rotational speed and direction of a selected motor of said plurality of motors;
    a plurality of surgical hand held cutting apparatuses comprising a first disposable hand assembly adapted to cut tissue at a first range of rotational speeds and a second disposable hand assembly adapted to cut tissue at a higher range of rotational speeds; and
    a plurality of flexible drive shaft assemblies, each shaft assembly connecting a disposable hand assembly to a motor to transmit the rotational speed and direction of a motor shaft from a selected motor to a cutter member mounted in a selected disposable hand assembly.

2. A surgical tissue cutting assembly as claimed in claim 1 wherein said control means includes a foot pedal assembly with foot controlled selection means enabling a surgeon to selectively engage one of the motors of said plurality of motors to rotate a selected flexible drive shaft assembly and said cutter member of said disposable hand assembly.

3. A surgical tissue cutting assembly as claimed in claim 2 wherein at least one of said motors of said plurality of motors is adapted to rotate a first flexible drive shaft assembly at a rotational speed in the range of zero to 4,000+ revolutions per minute and at least one of said motors of said plurality of motors is adapted to rotate a second flexible drive shaft assembly at a rotational speed in the range of zero to 16,000+ revolutions per minute.

4. A surgical cutting assembly as claimed in claim 1 wherein one of said hand assemblies comprises:
    a cylindrical main housing having a proximal end and a distal end and a throughgoing lumen running along the central axis of the housing, said proximal end and said distal end of said main housing being recessed and said housing forming a handpiece;
    a collet rotatably mounted within the distal end of said main housing and provided at its distal end with a deformable shaft receiving tip;
    cutting means comprising a cutting shaft and a cutting tip mounted within the shaft receiving tip of said collet;
    retaining means disposed on the distal tip of said collet to deform the shaft receiving tip of said collet to bias the tip against said cutting means shaft; and,
    a flexible drive shaft for bidirectionally rotating said collet, said flexible drive shaft being positioned in the throughgoing lumen in said cylindrical main housing and mounted to said collet to drive said collet.

5. A surgical tissue cutting assembly as claimed in claim 1 wherein quick coupling means is disposed at the proximal end of each of said flexible drive shaft assembly for quickly connecting and disconnecting said flexible drive shaft to or from a selected motor of said plurality of motors.

6. A surgical tissue cutting assembly as claimed in claim 1 wherein one of said hand assemblies comprises:
    a housing defining a central lumen;
    a conical nose cone means secured to the distal end of said housing;
    a stationary outer cutter tube mounted to said nose cone means and extending from the distal end of said nose cone means, said cutting tube defining a blade aperture at the distal end of said outer cutter tube;
    an inner cutter tube rotatably mounted within said outer cutter tube including a gear mounted on said inner cutter tube;
    gear means mounted within said hand assembly handpiece housing for driving said inner cutter tube gear with respect to said outer cutter tube causing blade means on said inner cutter tube to move past said aperture in said outer cutter tube; and,
    a flex-drive mounted to said gear means and a motor to transmit the drive from a motor shaft of said motor.

7. An external drive with a plurality of removably mounted disposable surgical hand cutting assemblies comprising:
    a housing control unit comprising a plurality of motors, each of said motors being capable of driving a selected removably mounted disposable surgical hand cutting assembly at a range of different rotational speeds;
    at least one disposable surgical hand cutting assembly being capable of debriding hard tissue at a first speed and a second disposable surgical hand cutting assembly being capable of debriding soft tissue at a second different speed;
    flexible shaft means for transmitting the torsional force from a selected motor to a selected disposable surgical hand cutting assembly; and,
    quick connect means disposed on the end of said flexible shaft means to quickly connect said selected disposable surgical hand cutting assembly to one of the motors of said plurality of motors.

8. An external drive with a plurality of removably mounted disposable surgical hand cutting assemblies as claimed in claim 7 wherein each surgical hand cutting assembly includes a vacuum means mounted to a channel formed within a surgical handpiece of said disposable surgical hand cutting assembly for removing tissue cut from a surgical site, and fluid delivery means disposed within said surgical handpiece for delivering sterile surgical fluid to said surgical site.

9. An external drive with a plurality of removably mounted disposable surgical hand cutting assemblies as claimed in claim 8 wherein said vacuum means comprises a vacuum tube and wherein said surgical handpiece comprises:

- a housing having a central lumen and a vacuum tube channel;
- a conical nose cone means secured to the distal end of said housing;
- a stationary outer cutter tube extending from the distal end of said nose cone means defining a blade aperture at the distal end of said outer cutter tube;
- an inner cutter tube with gear means mounted thereto rotatably disposed within said outer cutter tube with said inner cutter tube defining a blade means at the distal end thereof;
- gear means mounted within said handpiece housing engaging the inner cutter tube to rotate said inner cutter tube with respect to said outer cutter tube causing said blade means to move past said blade aperture in said outer cutter tube;
- a flexible shaft extending through said housing to engage and rotate said gear means driving said inner cutter tube; and
- a vacuum tube extending through said housing communicating with the proximal end of said inner cutter tube to vacuum away debris cut from a surgical site.

10. An external drive with a plurality of removably mounted disposable surgical hand cutting assemblies as claimed in claim 9 wherein said flexible shaft comprises a flexible coaxial cable having a round cross section with squared ends and a wire spirally disposed around the middle portion of said coaxial cable so that the ends of the coaxial cable are exposed.

11. An external drive with a plurality of removably mounted disposable surgical hand cutting assemblies as claimed in claim 10 wherein said flexible coaxial cable is surrounded by a fluid impermeable sheath member.

12. An external drive with a plurality of selectively mounted disposable surgical handpiece assemblies for cutting tissue, comprising:

- a housing control unit comprising a plurality of motors, each of said motors being capable of driving a selected surgical handpiece assembly at a different range of rotational speeds;
- one of said selectively mounted disposable surgical handpiece assemblies being capable of debriding hard tissue with another of said surgical handpiece assemblies being capable of cutting soft tissue;
- flexible shaft means for transmitting the torsional force from a selected motor to a surgical handpiece included in each surgical handpiece assembly; and
- quick connect means disposed on an end of said flexible shaft means to quickly connect said surgical handpiece to a selected motor of said plurality of motors.

13. An external drive with a plurality of relatively mounted disposable surgical handpiece assemblies for cutting tissue as claimed in claim 12 wherein said flexible shaft means comprises a flexible coaxial cable having a round cross section with squared ends and a wire spirally disposed around the middle portion of said coaxial cable so that the ends of the coaxial cable are exposed.

14. A surgical tissue cutting and debriding system, comprising:

- a motor control unit comprising a plurality of motors, each of said motors being adapted to operate in a different operating range of rotational speeds;
- control means for controlling the rotational speed and direction of a selected motor of said plurality of motors;
- a plurality of surgical hand cutter means comprising a first surgical hand assembly adapted to debride tissue at a first high range of rotational speeds and a second surgical hand assembly adapted to debride tissue at a second lower range of rotational speeds; and
- a plurality of flexible shaft assemblies, each shaft assembly of said plurality of shaft assemblies being selectively connected to a surgical hand assembly of said plurality of surgical hand assemblies for transmitting the rotational speed and direction of each motor shaft of said plurality of motors to each surgical hand assembly.

15. A surgical tissue cutting and debriding system as claimed in claim 14 wherein said control means further comprises foot controlled selection means enabling the surgeon to selectively engage one of the motors of said plurality of motors to rotate a selected flexible shaft assembly and hand assembly.

16. A surgical tissue cutting and debriding system as claimed in claim 15 wherein at least one of said motors of said plurality of motors in said motor control unit is adapted to bi-directionally rotate a shaft assembly at a rotational speed in the range of zero to 4,000+ revolutions per minute and at least one of said motors of said plurality of motors in said motor control unit is adapted to bi-directionally rotate a flexible shaft assembly at a rotational speed in the range of zero to 16,000+ revolutions per minute.

17. A surgical tissue cutting and debriding system as claimed in claim 16 wherein each of said flexible shaft assemblies comprises a coaxial wire member and a second wire member wrapped spirally around the middle of said coaxial wire member so that both ends of said coaxial wire member are exposed.

18. A surgical tissue cutting and debriding system as claimed in claim 14 wherein at least one of said hand assemblies further comprises a bi-directional, rotating blade means at a proximal end thereof and vacuum means adjacent said blade means for vacuuming debrided tissue away from a surgical site and fluid delivery means in fluid communication with said rotating blade means for delivering sterile surgical fluid to a surgical site.

\* \* \* \* \*